(12) United States Patent
Yi et al.

(10) Patent No.: US 9,360,660 B2
(45) Date of Patent: Jun. 7, 2016

(54) METHODS AND APPARATUS FOR LASER SCANNING STRUCTURED ILLUMINATION MICROSCOPY AND TOMOGRAPHY

(71) Applicant: Northwestern University, Evanston, IL (US)

(72) Inventors: Ji Yi, Chicago, IL (US); Vadim Backman, Chicago, IL (US); Qing Wei, Evanston, IL (US); Hao F. Zhang, Deerfield, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 42 days.

(21) Appl. No.: 13/902,288

(22) Filed: May 24, 2013

(65) Prior Publication Data

US 2013/0314717 A1    Nov. 28, 2013

Related U.S. Application Data

(60) Provisional application No. 61/651,264, filed on May 24, 2012.

(51) Int. Cl.
*G02B 21/06* (2006.01)
*G02B 21/00* (2006.01)
(Continued)

(52) U.S. Cl.
CPC ........ *G02B 21/0032* (2013.01); *G01B 9/02014* (2013.01); *G01B 9/02044* (2013.01);
(Continued)

(58) Field of Classification Search
CPC ........... G02B 21/0032; G02B 21/0024; G02B 21/0048; G02B 21/0056; G02B 21/06; G01B 9/02044; G01B 9/02091; G01B 9/02069; G01B 9/02014; G01N 21/64; G01N 21/45; G01N 21/4795; G01N 2021/1787; G01N 2021/456; G01N 2201/067; G01N 2201/0691
See application file for complete search history.

(56) References Cited

U.S. PATENT DOCUMENTS

2002/0048025 A1 *   4/2002  Takaoka .................. 356/497
2007/0278389 A1 * 12/2007  Ajgaonkar et al. ........ 250/221
(Continued)

OTHER PUBLICATIONS

Chen et al "Hacking the optical diffraction limit: Review on recent developments of fluorescence nanoscopy", Chinese Science Bulletin, Jun. 2011, vol. 56, No. 18:1857-1876, 20 pages.
Lu et al, "Super-Resolution Laser Scanning Microscopy through Spatiotemporal Modulation", Nano Letters, 2009, vol. 9, No. 11, 3883-3889, Department of Molecular and Cellular Biology, Center for Brain Science, Department of Chemistry and Chemical Biology, Harvard University, 7 pages.

*Primary Examiner* — Tarifur Chowdhury
*Assistant Examiner* — Michael P Lapage
(74) *Attorney, Agent, or Firm* — Hanley, Flight and Zimmerman, LLC (57) ABSTRACT

Certain examples provide a structured illumination microscopy system. The example system includes a laser source to generate excitation illumination directed toward a target. The example system includes a modulator to modulate the excitation illumination temporally in a controllable spatial pattern to be constructed on the target object to provide sub-diffractional resolution in a lateral direction with respect to the target. The example system includes two synchronized laser scanning mirror units in confocal arrangement, the laser scanning units to be synchronized and controlled by a computing device, a first of the scanning mirror units to receive the modulated excitation illumination and project the modulated excitation illumination on the target object and a second of the scanning mirror units to receive emission fluorescence from the target and project the emission fluorescence. The example system includes a detector to collect emission fluorescence from the target via the second of the scanning mirror units.

19 Claims, 9 Drawing Sheets

(51) Int. Cl.
*G01N 21/64* (2006.01)
*G01B 9/02* (2006.01)
*G01N 21/45* (2006.01)
*G01N 21/47* (2006.01)
*G01N 21/17* (2006.01)

(52) U.S. Cl.
CPC ........ *G01B9/02069* (2013.01); *G01B 9/02091* (2013.01); *G01N 21/45* (2013.01); *G01N 21/4795* (2013.01); *G01N 21/64* (2013.01); *G01N 21/6458* (2013.01); *G01N 2021/1787* (2013.01); *G01N 2021/456* (2013.01); *G01N 2201/067* (2013.01); *G01N 2201/0691* (2013.01)

(56) References Cited

U.S. PATENT DOCUMENTS

| | | | |
|---|---|---|---|
| 2007/0291277 A1* | 12/2007 | Everett et al. | 356/497 |
| 2009/0073522 A1* | 3/2009 | Thomas | 359/22 |
| 2009/0238222 A1* | 9/2009 | Dantus et al. | 372/22 |
| 2011/0043661 A1* | 2/2011 | Podoleanu | 348/239 |
| 2011/0182529 A1 | 7/2011 | Kempe et al. | |
| 2011/0267688 A1* | 11/2011 | Kleppe | G02B 21/0036 359/385 |

\* cited by examiner

METHODS AND APPARATUS FOR LASER SCANNING STRUCTURED ILLUMINATION MICROSCOPY AND TOMOGRAPHY

CROSS-REFERENCE TO RELATED APPLICATIONS

The present application claims priority to U.S. Provisional Application No. 61/651,264, filed on May 24, 2012, which is herein incorporated by reference in its entirety.

STATEMENT REGARDING FEDERALLY SPONSORED RESEARCH OR DEVELOPMENT

This invention was made with government support under Grant Numbers R01CA128641, R01EB003682, R01EY019951, and RC4EY021357 awarded by the National Institute of Health and Grant Numbers CBET-0937987 and CBET-1055379 awarded by the National Science Foundation. The government has certain rights in the invention.

FIELD OF THE DISCLOSURE

This disclosure relates generally to laser scanning microscopy and tomography, and, more particularly, to laser scanning structured illumination microscopy and tomography.

BACKGROUND

Resolution of optical microscopes is limited by diffraction, as explained by the theory of Fourier optics, wherein a resolution limit for a microscope is given by the extent of its optical transfer function, a normalized Fourier transform of a point spread function. For many biological structures and molecular processes, however, their length scale is below a diffraction limit (e.g., a point at which an aperture or opening is too small to allow light to pass through for clear image resolution), preventing them from being resolved with conventional optical microscopes.

The following detailed description of certain embodiments of the present invention will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Overview

In optical microscopy, such as laser scanning microscopy (LSM) or confocal LSM (CLSM), a focused beam of a laser is scanned over a sample, and a reflected intensity is displayed as a function of position to create a digital reflected light image of the sample. Scanning a focused laser beam facilitates acquisition of digital images with high resolution determined by a position of the beam rather than a pixel size of a detector.

Using confocal laser scanning microscopy allows high-resolution optical images to be obtained with depth selectivity. In-focus images can be acquired from selected depths (e.g., optical sectioning). Images are acquired point-by-point and reconstructed with a computer, allowing three-dimensional reconstructions of topologically complex objects, for example. Thus, both surface profiling of opaque samples and imaging of interior structures of non-opaque samples can be facilitated. While a conventional microscope "sees" as far as light can penetrate into a sample, a confocal microscope "sees" images one depth level at a time.

In a confocal laser scanning microscope, a laser beam passes through a light source aperture and then is focused by an objective lens into a small (e.g., diffraction limited) focal volume within or on the surface of a sample. Scattered and reflected laser light as well as fluorescent light from the illuminated spot on or in the sample is then re-collected by the objective lens. A beam splitter separates a portion of the light into a detector, which may also have a filter to selectively pass fluorescent wavelengths while blocking the original excitation wavelength. After passing a pinhole aperture, the light intensity is detected by a photodetection device (e.g., a photomultiplier tube, avalanche photodiode, etc.), to transform the light signal into an electrical signal that is recorded by a computer.

The detector aperture obstructs light that is not coming from the focal point. The out-of-focus light is suppressed; most of the returning light is blocked by the pinhole, which allows obtaining images of planes at various depths within the sample. Information can be collected from different focal planes by raising or lowering a microscope stage or objective lens. A computer can generate a three-dimensional picture of a sample by assembling a stack of two-dimensional images from successive focal planes.

Thus, confocal microscopy, in which one focus or image point of a lens is the same as one focus/image point of a next lens, provides a capacity for direct, noninvasive, serial optical sectioning of intact, thick, living specimens with improvement in lateral resolution.

Resolution of an optical imaging system, such as a laser scanning microscopy system, can be limited by lens imperfection, misalignment, diffraction, etc. At small apertures, most modern lenses are affected primarily by diffraction.

Certain examples provide realization of structured illumination microscopy (SIM) on a lasing scanning scheme (e.g., laser scanning structured illumination microscopy (LSSIM)) to achieve sub-diffractional lateral resolution imaging. Laser scanning plays a role in biomedical microscopy and has a number of advantages that may be unattainable by wide field illumination microscopy. Although structural illumination (SI) has been previously implemented in wide field microscopy to increase spatial resolution by a factor of two, certain examples combine SI with a laser scanning scheme. Moreover, in comparison to other super-resolution modality (e.g., stimulated emission depletion (STED), photoactivated localization microscopy (PALM), stochastic optical reconstruction microscopy (STORM), etc.), SIM is more tolerable in terms of a choice of contrast agents. For example, STED, PALM and STORM rely on photo-switchable fluorophores, while SIM involves a common fluorescent stain or even endogenous scattering contrast without any contrast agents.

Microscopy and tomography modalities adapt a laser scanning scheme, such as confocal microscopy, non-linear microscopy (e.g., two-photon, second-harmonic generation, stimulated Raman scattering, stimulated absorption, etc.), optical coherence tomography and photo acoustic microscopy/tomography, etc. An advantage of a laser scanning scheme over wide field illumination is a capability of focusing a large amount of optical power within a diffraction limit focus spot so that a signal-to-noise ratio can be drastically enhanced. For microscopy modalities that rely on non-linear effects (e.g., two/multi-photon microscopy), a laser scanning scheme may be the only option. Thus, SI adapted for the laser scanning scheme paves the way for super-resolution imaging in all above microscopy modalities, which would have significant impact on biomedical research.

Optical coherence tomography (OCT) is a three-dimensional imaging modality with micrometer-level resolution and millimeter-level penetration depth. Illumination on some OCT systems is implemented by a confocal scheme that allows a focused Gaussian beam to scan laterally. Lateral resolution and depth of focus can be determined by a full width at half-maximum (FWHM) and Rayleigh range of the beam, which pose a trade-off. Using an objective lens with a higher numerical aperture, resolution can be increased, but depth of focus is shortened. To overcome this limitation, a scattering problem can be numerically solved to recover resolution out of the Rayleigh range without additional hardware. Another approach is to modify a beam profile that extends the depth of focus while maintaining the resolution, for example, to create a Bessel beam illumination. With those improvements, however, the lateral resolution is still constrained by the diffraction limit.

Certain examples can be applied with both fluorescent and non-fluorescent media (whereas other super resolution technologies only operate with respect to fluorescence). Certain examples work with nonlinearly excited optical microscopy, as well as with linearly excited optical signals.

Certain examples provide systems, methods and apparatus for laser scanning structured illumination microscopy and tomography (LSSIM/T) to achieve sub-diffractional resolution in lateral direction. By modulating laser scanning illumination or excitation temporally, a controllable spatial pattern can be constructed on target object(s) so that sub-diffractional resolution in a lateral direction can be achieved in microscopy modalities with a laser scanning scheme. A linear scanning focus beam can translate the temporal modulation into the spatial pattern on the object(s). When the pattern is periodic, a spatial frequency in a Fourier space of an object is shifted so that a high spatial frequency can be detected, which enhances resolution beyond a resolution limit.

By applying the laser scanning structured illumination, the lateral resolution of OCT can exceed the diffraction limit. This OCT modality is referred to herein as structured illumination optical coherence tomography or structured interference optical coherence tomography (SIOCT). SIOCT can be used to enhance lateral resolution beyond the diffraction limit. In certain examples, a sinusoidal pattern is created on an interferometric beam with a reference intensity temporally modulated. In the Fourier domain, high spatial frequencies are shifted into a detectable range, which enhances the lateral resolution beyond the diffraction limit by a factor of, for example, 2. For example, the lateral resolution of SIOCT can be characterized in a study as ~5.5 µm), surpassing the diffraction limit ~9.6 µm as in conventional Fourier-domain optical coherence tomography.

By tuning a periodic frequency of a temporal modulation, varying direction of a spatial pattern can be produced to implement structured illumination. A number of modulation periods during one B-scan can be configured to be a non-integer so that a fixed phase shift is created between consequential B-scans. With a raster scan scheme, the phase shift produces another periodic pattern on the other direction so that a direction of an associated two-dimensional (2D) illumination structure can be tuned freely.

In certain examples, an add-on optical module can be built to be attached to existing laser scanning microscopes regardless of manufacturer.

Traditionally, researchers observing biological samples have not been able to resolve structures smaller than half the wavelength due to a physical limitation called the "diffraction limit." During the last three decades, numerous advanced optical techniques have been demonstrated to break the diffraction limit and visualize sub-diffractional structures, such as near-field scanning optical microscopy (NSOM), STED, PALM, SIM, STORM, etc.

NSOM collects an evanescent wave to achieve high resolution within a close vicinity of a probing tip, usually on an order of several tens of nanometers. STED, PALM and STROM rely on photoswitchable fluorophores. By controlling conditions for the fluorophores to be activated, resolution can be improved. SIM uses another approach. It projects a periodic illumination pattern on the sample, and the high spatial frequency components of the sample together with the illumination pattern produces moire fringes. In the Fourier space, the periodic pattern shifts the high spatial frequency into a detectable range thereby ultimately enhancing the resolution by twofold beyond the diffraction limit. The resolution can be enhanced even higher (e.g., up to ~50 nm) with a nonlinear structured illumination mode, for example.

Although SIM can be realized by a wide-field illumination, SIM can alternatively be realized by a confocal scheme. For example, a charge-coupled device (CCD) camera or a complementary metal oxide silicon (CMOS) camera can be used to integrate an entire 2D confocal image while a scanning beam is temporally modulated. In another example, a single photo detector, such as a photo-multiplier tube (PMT) or an avalanche photodetector, can be used to detect the signal. Advantages of the single detector over a 2D CCD or CMOS camera include high sensitivity and ease of implementation. Additionally, SIM can be combined with a laser scanning scheme, for example.

Realizing SIM in a confocal scheme can have a profound effect on biomedical research. Most microscopy and tomography modalities adapt a laser scanning scheme, such as confocal microscopy, non-linear microscopy (two-photon, second-harmonic generation, stimulated Raman scattering, stimulated emission, etc.), optical coherence tomography, and photo acoustic microscopy/tomography, etc. An advantage of laser scanning scheme over wide field illumination is a capability of focusing a large amount of optical power within a diffraction-limited focal spot so that a signal-to-noise ratio can be drastically enhanced. In the case of microscopy, modalities that are based on non-linear optical effects as a source of contrast, a laser scanning scheme is the only option. Moreover, comparing other modalities (e.g., STED, PALM and STORM), SIM is more tolerable in terms of the choice of contrast agents. Indeed, STED, PALM and STORM rely on photo-switchable fluorophores, while SIM involves common fluorescent stains or even endogenous scattering contrast without any contrast agents. Thus, realizing super-resolution using laser scanning SIM can have a significant impact on a spectrum of biomedical research.

Brief Description

Certain examples provide a structured illumination microscopy system. The example system includes a laser source to generate excitation illumination directed toward a target object. The example system includes a modulator to modulate the excitation illumination temporally in a controllable spatial pattern to be constructed on the target object to provide sub-diffractional resolution in a lateral direction with respect to the target object. The example system includes two synchronized laser scanning mirror units in confocal arrangement, the two laser scanning units to be synchronized and controlled by a computing device, a first of the two scanning mirror units to receive the modulated excitation illumination and project the modulated excitation illumination on the target object and a second of the two scanning mirror units to receive emission fluorescence from the target object and project the emission fluorescence. The example system includes a detector to collect emission fluorescence from the target object via the second of the two scanning mirror units for processing to form an image.

Certain examples provide a structured interference optical coherence tomography system. The example system includes a laser source to generate excitation illumination directed toward a target object. The example system includes a modulator to modulate the excitation illumination temporally in a controllable spatial pattern to be constructed on the target object to provide sub-diffractional resolution in a lateral direction with respect to the target object. The example system includes two laser scanning units in confocal arrangement, the laser scanning units synchronized and controlled by a computing device. The example system includes a detector to collect emission illumination from the target object via the two laser scanning units for processing to form an image.

Example methods of using these systems are also provided.

Instrumentation

Certain examples provide a temporal modulation module to enhance lateral resolution beyond a diffraction limit by SIOCT, while depth of focus is kept the same. Structured illumination (also referred to as structured interference) can be applied with wide-field illumination along with the image of a periodic grating projected on a subject. High spatial frequency components of a sample together with an illumination pattern produce moiré fringes. In the Fourier space, a delta function resulted from periodic pattern shifts high spatial frequencies into a detectable range. With an extended spatial frequency, resolution is enhanced, for example, two-fold beyond the diffraction limit. Alternatively, structured illumination can be realized in a confocal scheme with a scanning beam.

Figure 1:
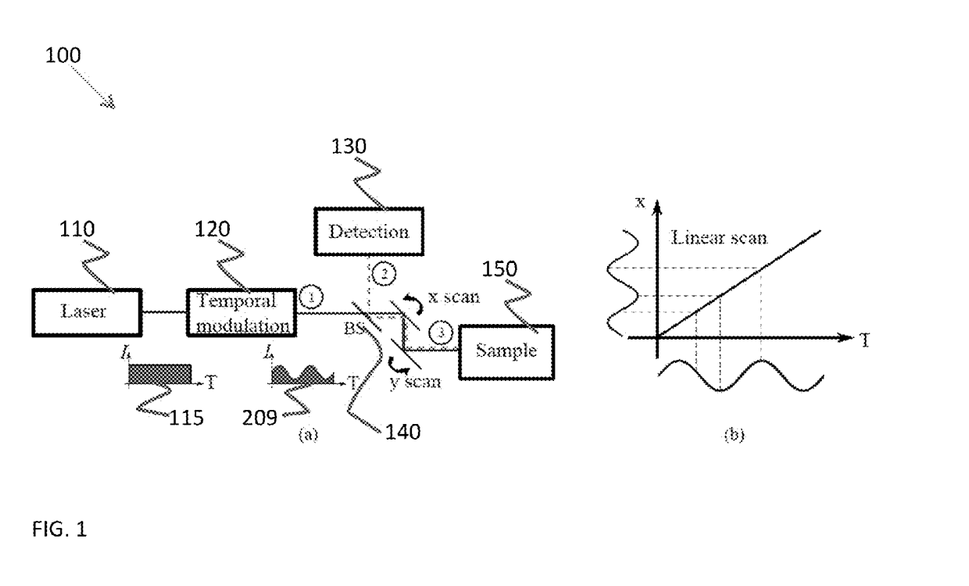
FIG. 1A illustrates an example system for laser scanning structured illumination.
FIG. 1B illustrates an example translation of temporal modulation into a spatial illumination pattern.

As shown in FIG. 1A, when a focal spot is linearly steered along a lateral direction, a temporally modulated intensity is transformed to a spatial pattern as in wide-field structured illumination. In OCT, rather than modulating the incident intensity on a sample, the reference intensity can be modulated due to the interferometric principle.

As shown in FIG. 1A, intensity is modulated temporally in a periodic manner such as a sinusoidal form. When a raster linear scan is applied to obtain a lateral map of a specimen, the temporal modulation is translated into a spatial pattern as in wide field structured illumination (see, e.g., FIG. 1B). The detector continuously collects signals for post-processing. FIG. 1A shows an example microscopy system 100 that integrates a temporal modulator 120 after a laser source output 110 (see position 1 in FIG. 1A). The temporal modulator 120 can also be installed at other locations on an optical path such as in front of a detector 130 (see position 2, before detection 130, in FIG. 1A) or before a sample 150 (see position 3, before sample 150 illumination, in FIG. 1A). The temporal modulation can be realized in different ways using the temporal modulator 120 to take a laser output 115 and introduce temporal modulation into that output 115 to provide a modulated output 125. For example, an opto-mechanical chopper and an optical scanner (e.g., galvo or polygon mirror) can be used to create periodic modulation, or an electro-optic modulator can be provided for a higher speed, etc. A beam splitter 140 including one or more mirrors facilitates an x and y scan of the sample 150 to provide data to the detector 130, for example.

As illustrated, for example, in FIG. 1B, under a raster linear scan, the temporal modulation is transformed into a spatial illumination pattern. A frequency of the temporal modulation determines a period of the pattern.

Example Laser Scanning Structured Illumination Methods and Systems

A linear structured illumination involves three periodic patterns with 120° rotation angle to each other. Each pattern uses three phases to reconstruct extended spatial frequency components. As discussed above, a different pattern can be realized by tuning the temporal modulation frequency. Assuming the raster scan covers a square dimension of 1 μm, sampling points in each direction are n, and a time required to finish one line scan is T seconds. The following equation can be used to realize a vertical strip pattern with a period of d μm, $$f = 1/dT. \tag{Eq. 1}$$

Figure 2:
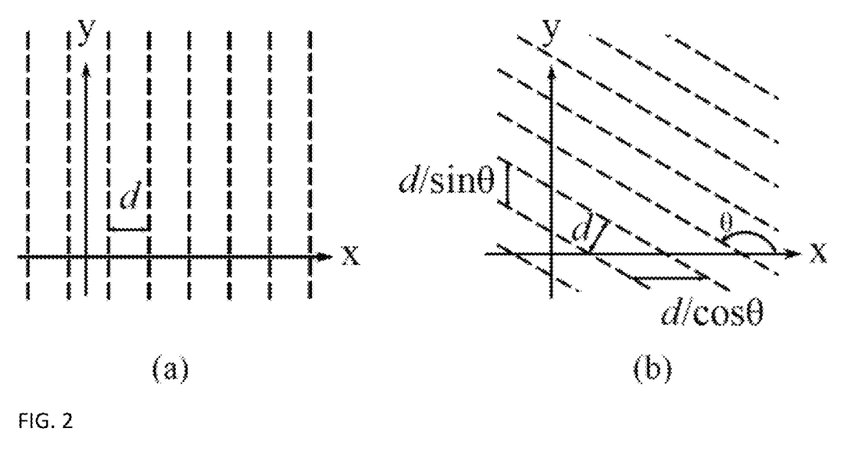
FIGS. 2A and 2B depict example temporal modulation frequency tuning for spatial illumination patterns.

As shown in FIG. 2A, assume that a raster scan line is along an x direction. If one scan line covers a number of complete modulation periods, the same pattern will be repeated on the next x scan and ultimately create a vertical strip pattern when a y scan is completed. A next 2D pattern can start with a fix phase delay since a precise time delay between two sequential scan can be controlled.

Similarly, to realize modulation pattern with $\theta \pm 120°$ rotation to the vertical strip, one can specify the modulation frequency as:

$$f = \left(\cos\theta \pm \frac{\sin\theta}{n}\right) 1/dT. \tag{Eq. 2}$$

The first term is to elongate the temporal period so that the pattern period can be kept constant as d μm, shown, for example, in FIG. 2B. The second term is to introduce certain phase delay between sequential raster scan lines, which produces a periodic pattern in a y direction as well.

FIGS. 2A and 2B depict example temporal modulation frequency tuning for spatial illumination patterns. In FIG. 2A, a vertical strip pattern can be projected on the object when the periods of temporal modulation on one x-scan corresponds to an integer. In FIG. 2B, an angled pattern can be produced with additional phase shift in one x-scan. Once structured illumination is realized, data processing to achieve super-resolution can be performed according to a SIM algorithm, for example.

In certain examples, a variety of laser scanning imaging modalities can be employed with temporal modulation to improve microscopy/tomograph resolution including structured illumination confocal microscopy (SICM), structured illumination optical coherence tomography (SIOCT), etc., to demonstrate the LSSIM/T.

Figure 3A:
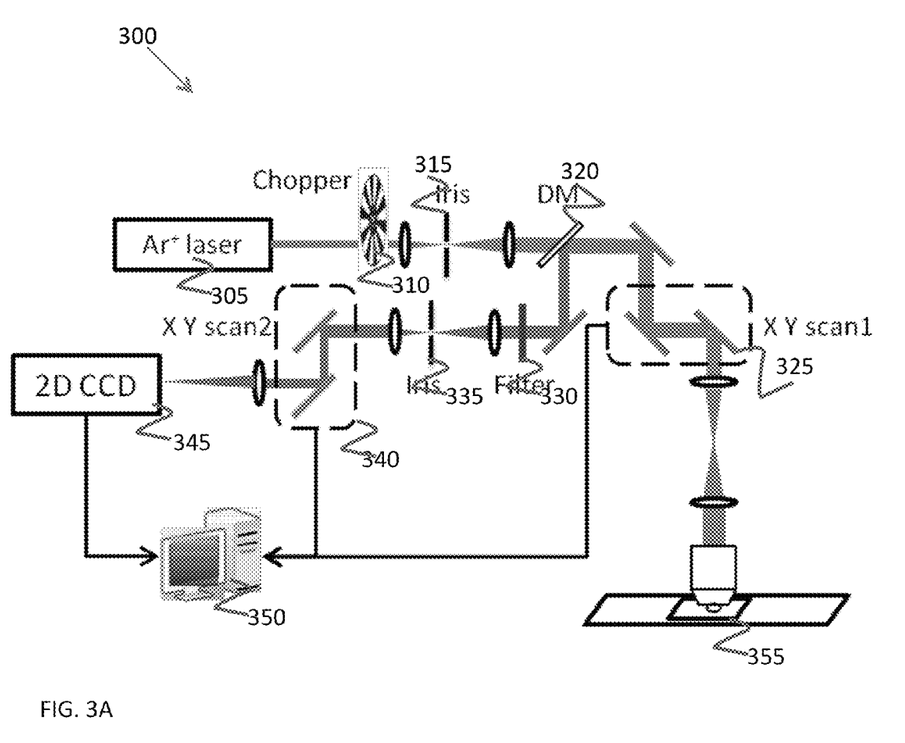
FIG. 3A depicts an example structured illumination confocal microscopy system.

FIG. 3A depicts an example laser scanning confocal fluorescent SIM (e.g., an SICM or LS-f-SIM) system 300. A laser 305, such as a continuous wave (CW) 488-nm argon-ion laser (e.g., a 161C-410-21 by Spectra Physics), is used as a laser source to excite a fluorophore in laser scanning confocal fluorescent SIM. The resulting fluorescence signal is continuously recorded by a two-dimensional CCD 345 or other detector such as a CMOS camera. A filter 330 and iris 335 positioned with an x y axis linear scanning mirror unit 340 (e.g., a pair of rotatable mirrors to steer the laser beam such as piezo-driven galvo mirrors (GM), QS-7, by Nutfield Technology, Windham, N.H., or other rotation mechanisms such as resonance scanning mirrors, etc.) before the 2D CCD 345 is in conjugation with the flying focal point of illumination on a sample 355, which forms a confocal scheme.

An optical chopper 310 (e.g., an MC2000 chopper by Thorlabs, Inc., or other rotating disk with masks positioned to block the light and introduce light intensity modulation when spinning in the beam, etc.) is installed after the laser output 305 and modulates the excitation intensity temporally to realize structured illumination together with an x y axis linear scanning mirror unit 325 in conjunction with an iris 315 and dichroic mirror 320. The x-y scanning unit 340 is identically synchronized with the x-y scan 325, and, thus, the image of the iris 335 can be projected to the 2D CCD camera 345, which keeps the exposure during the full 2D scanning period. The point spread function passing the iris can be preserved. Other methods can be adopted to modulate the intensity with a faster speed and a higher sinusoidal quality, for example, by using an electro-optic intensity modulator.

In the example system 300, a dichroic mirror (DM) 320 is used to separate the excitation and emission light. The CMOS or CCD 345 is used to collected fluorescent signal. The iris 335 before the CCD/CMOS/PMT 345 is conjugated with the flying focal point on the sample 355 to form a confocal microscope. The laser scanning unit(s) 325, 340 and the CCD/CMOS/PMT 345 readout are synchronized and controlled by a central computer 350. For example, two laser scanning units are synchronized and controlled by a computing device, such as a central personal computer (PC) 350. For each two dimensional scanning, the CCD 345 is exposed continuously, for example.

Figure 3B:
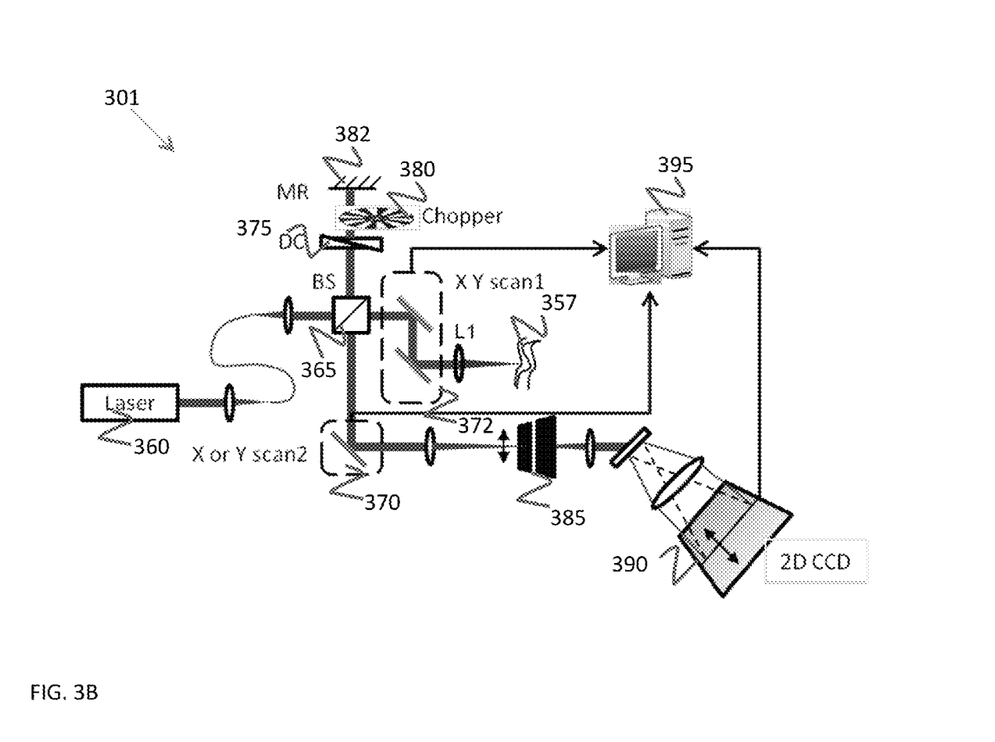
FIG. 3B shows an example structured illumination optical coherence tomography system.

FIG. 3B shows an example SIOCT system 301. The example system 301 can be based on free-space optics and/or fiber optics, for example. An optical modulator (e.g., chopper) 380 and/or other beam modulator (e.g., mechanical, electrical and/or optical) can be applied to modulate light from a laser 360 in the system 301, for example.

The example system 301 includes a laser 360 imaging an object 357. In FIG. 3B, a Fourier domain optical coherence tomography (FDOCT) is adopted. A cube beamsplitter (BS) 365 forms an open space Michelson interferometer, for example. A reference arm includes a dispersion control (DC) 375, a galvanometer mirror 382, and an optical chopper 380 for temporal intensity modulation. In certain examples, the chopper 380 may be located elsewhere in the system 301, such as immediately after the laser 360, between the beamsplitter 365 and the mirror 382, etc.

An interference spectrum is collected by a spectrometer 385 coupled with a 2D CCD camera 390 (or other detector such as a CMOS camera, PMT, etc.). A second scanning mirror unit 372 is synchronized with a fast scanning mirror in a first x-y scan mirror unit 370, for example.

Illumination is generated by a supercontinuum source (e.g., SuperK, NKT) with, for example, bandwidth from 650-800 nm, yielding an axial resolution of about 2 μm in air. A theoretical Gaussian focus beam has a waist of ~10 μm, for example. A B-scan rate is 10 frames per second and a period of the illumination pattern is configured to be around 12 μm, for example.

Similar to the LS-f-SIM, the second x or y scanning unit 372 is synchronized with the first x-y scanning unit 370. In SIOCT, a spectrograph 385 is used to detect the signal. Returning light is focused on a one dimensional entrance slit and moves along the slit as the x or y scanning is performed on the sample 357. At each position, the spectrum is dispersed at one direction of the 2D CCD camera 390 and the other direction is designated for either the x or y scan. Readout from the spectrometer 385 and CCD 390 are synchronized and controlled by a computing device 395, for example.

Figure 4:
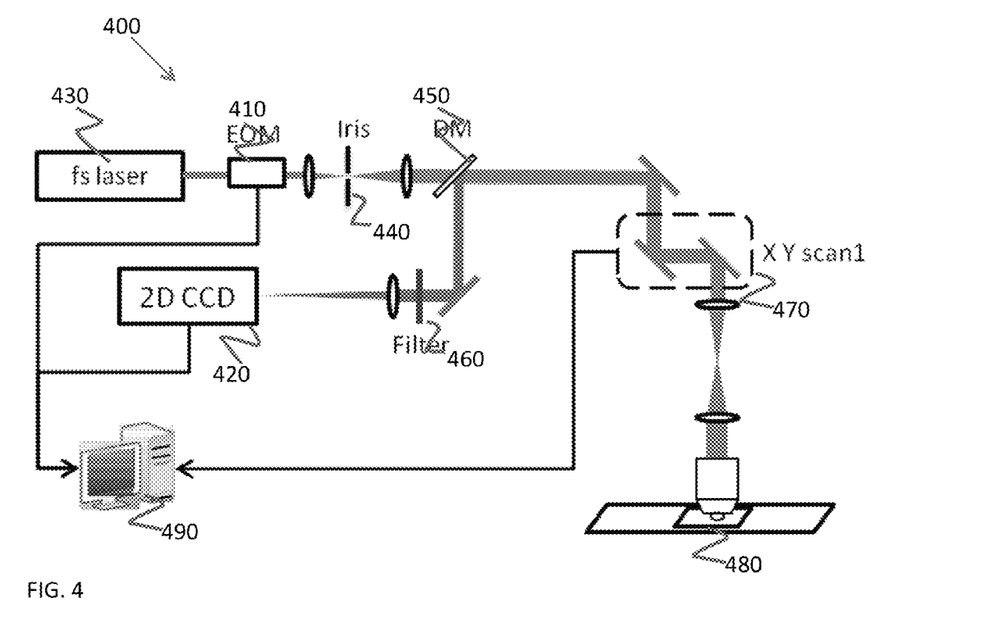
FIG. 4 shows an example multi-module structured illumination microscopy/tomography system.

FIG. 4 shows an example multi-photon structured illumination microscopy/tomography system 400 (e.g., a multi-photon LS-SIM system) including laser scanning two photon fluorescence microscopy (LS-TPM), laser scanning second harmonic microscopy (LS-SHGM), and/or optical coherence tomography (OCT) for in vivo applications. These microscopy and tomography devices may be integrated into a single laser scanning system scheme 400 to utilize the LSSIM method to achieve super resolution, for example. Similar to LS-f-SIM, temporal illumination is provided by an electro-opto modulator (EOM) 410, which can modulate the light intensity by combining with a polarizer. Due to self-sectioning in a multi-photon process, detection is simplified and a second set of scanning mirror(s) can be removed. A 2D electron multiplying charge coupled device (EMCCD) camera 420 is installed to acquire a fluorescence signal during the 2D scanning process. Recording is restarted at the beginning of each 2D scan, for example.

For example, FIG. 4 illustrates an example multi-photon LS-SIM system 400 including a (e.g., femto-second) pulse laser illumination source 430. An electro-opto modulator 410 is used for intensity modulation, for example. An x-y laser scanning mirror unit 470 is used in conjunction with a dichroic mirror 450, an iris 440, and a filter 460 to facilitate scanning of a sample 480 using modulated laser light. A 2D CCD camera 420 (or other detector) is used to capture the images, for example. Image information is provided to a computer 490, for example.

In an example SICM system, fluorescent nanospheres (e.g., with diameter ~180 nm) can be used. Chopper frequencies can be configured differently so that the illumination pattern can be rotated as described above. Each pattern then collects three images with the pattern shifted 120° in phase, for example. Thus, in this example, nine frames are used to construct a SICM image. An enhancement of resolution between conventional confocal fluorescent microscopy and SICM is visually appreciable. Spheres that are not resolvable in conventional confocal fluorescent microscopy can be discriminated in an image obtained using SICM, for example.

Figure 5:
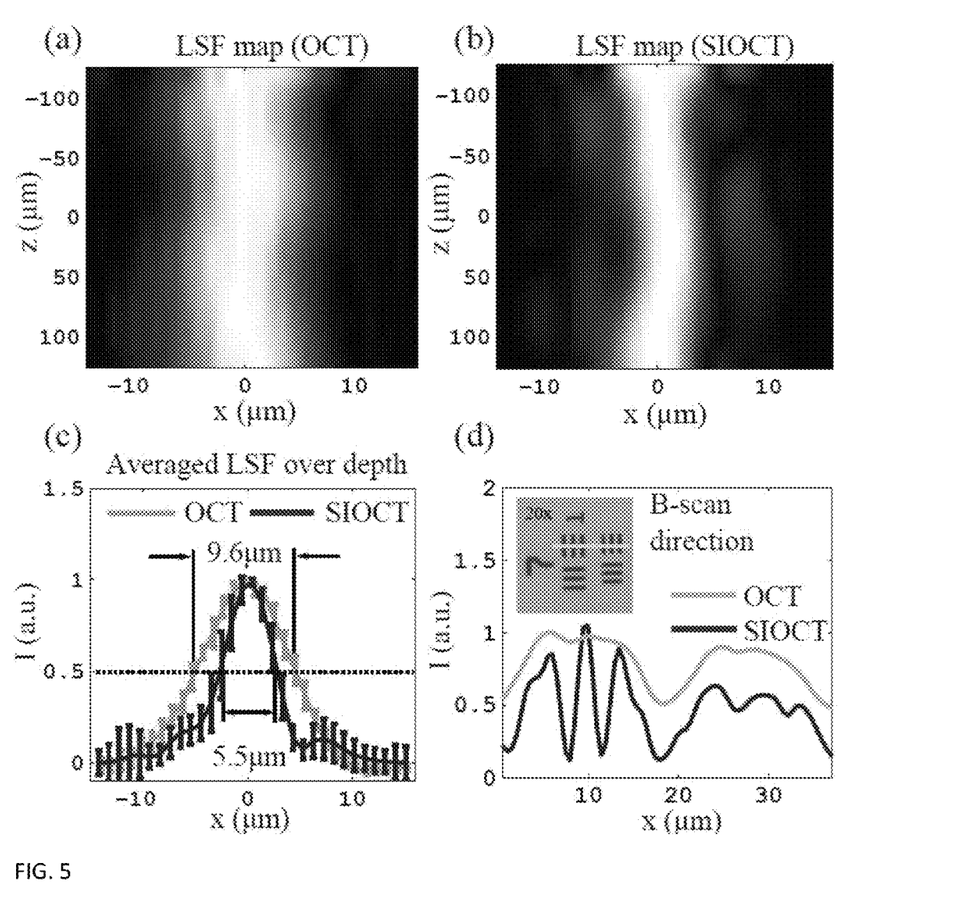
FIGS. 5A-5D illustrate example line spread function measurements.

In an example, to characterize a resolution of SIOCT, an edge of a large element (e.g., Group 2: element 1) on an AF-1951 resolution target is first imaged. A derivative of B-scan intensity from the edge is calculated as a line spread function (LSF). FIGS. 5A-5B illustrate example LSF measurements throughout a depth of focus of an objective lens in conventional OCT and SIOCT (e.g., ~200 μm). A curvy pattern is caused by slight asymmetry, for example. A target is shifted at various depths around a focal point, and a smooth map along z is obtained by an interpolation.

In an example, measurements are performed at depths of −112, −72, −28, 28, 64, 120 μm with respect to the focus spot. Each measured LSF is normalized to have a maximum value equal to 1. An averaged LSF over depth are compared in FIG. 5C, for example. A diffraction limited resolution is measured to be 9.6 μm while 5.5 μm in SIOCT, for example. Enhancement of the resolution is demonstrated in FIG. 5D. Each three strips of two small elements (e.g., Group 7: element 1 and 2) are resolved in SIOCT while the conventional OCT failed to provide sufficient resolution. Contrast of the Group 7: element 2 reduces due to together spacing.

Figure 6:
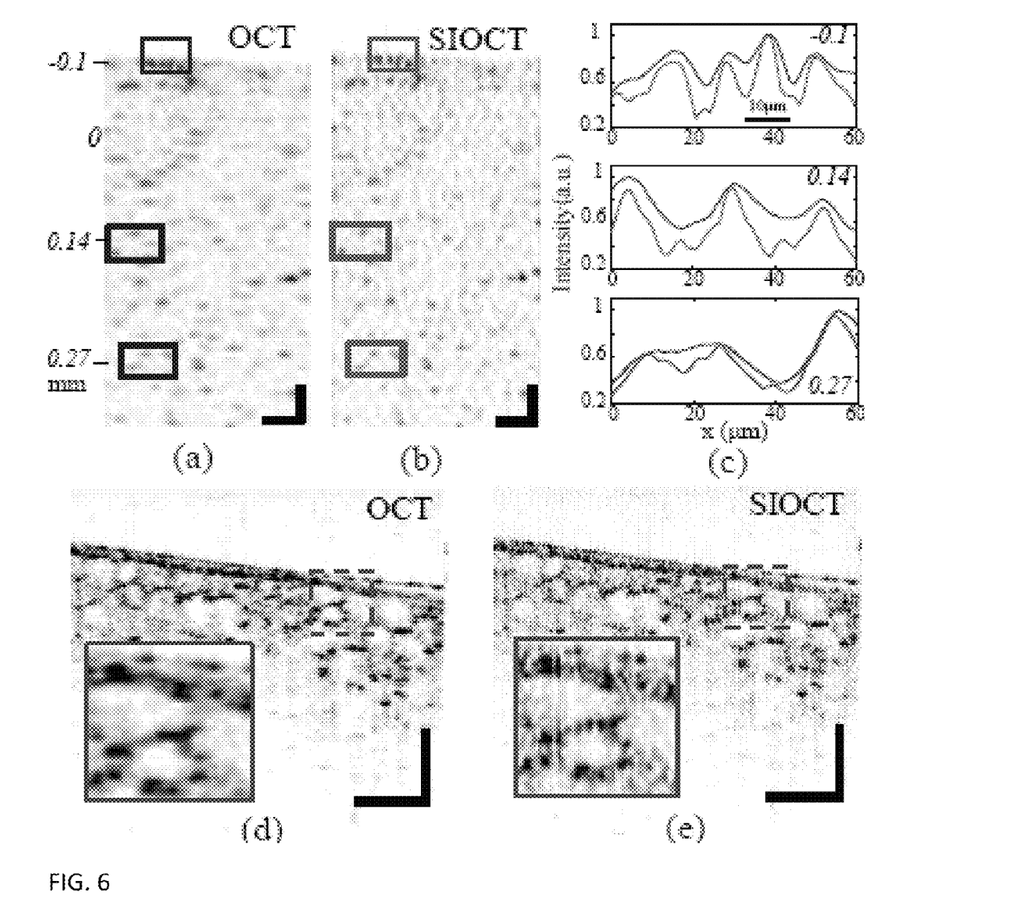
FIGS. 6A-6B show a comparison of the B-scan images.
FIG. 6C shows a comparison of mean intensity along depth from multiple areas.
FIGS. 6D-6E show structured illumination optical coherence tomography on a biological sample.

To further demonstrate the resolution enhancement, a phantom with 0.8 μm-1 μm diameter polystyrene microspheres can be composed. A sphere solution is dispersed in, for example, a hot Agarose gel solution which forms a clear solid phantom when cooling down. A size of the sphere is significantly smaller than the LSF so they are regarded as point scatterers, for example. FIGS. 6A-6B show a comparison of the B-scan images from conventional OCT and SIOCT. A mean intensity along depth from three areas is compared in FIG. 6C. To demonstrate the SIOCT on a biological sample, chicken adipose tissue can also be imaged with OCT and SIOCT as shown in FIGS. 6D-6E. In both cases, the enhancement of the lateral resolution is visually significant. FIG. 6C provides an example intensity summation over z from the squared areas in FIGS. 6A-6B.

In certain examples, a structured interference optical coherence tomography (SIOCT) is developed to enhance a lateral resolution beyond a diffraction limit. A sinusoidal pattern is projected on an interferometric beam with reference intensity temporally modulated. In the Fourier domain, high spatial frequencies are shifted into a detectable range which therefore enhances the lateral resolution beyond the diffraction limit by, for example, a factor of two. For example, the lateral resolution of SIOCT may be characterized as 5.5 m, surpassing the diffraction limit of 9.6 m as in conventional Fourier-domain OCT (FDOCT).

Optical coherence tomography (OCT) provides a three-dimensional (3D) imaging modality with micron-level resolution and millimeter-level penetration depth. Illumination on an OCT system is realized by a confocal scheme that allows a focused Gaussian beam to scan laterally. A full-width-half-maximum (FWHM) and Rayleigh range of the beam determines lateral resolution and depth of focus, which pose an inherent trade-off. By using an objective lens with a higher numerical aperture, the resolution can be increased but the depth of focus will be shortened. To overcome this limitation, different approaches have been developed.

One approach is to numerically solve the scattering problem that recovers the resolution out of the Rayleigh range without other additional hardware. Another approach is to modify the beam profile that extends the depth of focus while maintaining the resolution, for example, to create Bessel beam illumination. With those improvements, however, the lateral resolution is still constrained by the diffraction limit.

Certain examples provide systems, apparatus and methods to enhance the lateral resolution beyond the diffraction limit by realizing structured interference OCT, while the depth of focus is kept the same. Structured illumination provides wide field illumination with an image of a periodic grating projected on a subject. High spatial frequency components of the sample together with the illumination pattern produce moire fringes. In the Fourier space, a delta function resulting from the periodic pattern shifts the high spatial frequency into a detectable range. With the extended spatial frequency, the resolution is ultimately enhanced by two-fold beyond the diffraction limit, for example. Alternatively, the structured illumination can be realized in the confocal scheme with a scanning beam, for example.

As FIG. 3B shows, when the focal spot is linearly steered in the lateral direction, the temporally modulated intensity is transformed to a spatial pattern to the same effect as in wide field structured illumination. Typically, the incident intensity on the sample needs to be modulated, but in OCT the incident intensity can be the reference intensity that is modulated due to an interferometric principle, for example.

With structured interference, a B-scan image in SIOCT can be approximated as $$I(x,z)=I_0 R(x,z)[1+m\cos(k_m+\phi_0)], \quad |m|\leq 1 \tag{Eq. 3}$$

where x and z denote lateral and axial positions; I and R denote image intensity and a true reflectance of tissue with $I_0$ being illumination or incident intensity; m, $k_m$ and $\phi_0$ denote amplitude, frequency and initial phase of the illumination/modulation pattern, respectively. In SIOCT, the structured illumination or interference is on the lateral extent, which is independent of the axial profile obtained by an inverse Fourier transform (IFT) of the interference spectrum. Thus, the parameter z may be omitted from this point on. The spatial frequency distribution is the Fourier transform (FT) of the image intensity, $$\tilde{I}(k_x)/I_0 = \tilde{R}(k_x) + \frac{m}{2}e^{j\phi_0}\tilde{R}(k_x-k_m) + \frac{m}{2}e^{-j\phi_0}\tilde{R}(k_x+k_m), \tag{Eq. 4}$$

where $\tilde{I}$ denotes a FT of I (the tilde symbol is used to represent the FT throughout); $k_x$ denotes a spatial frequency along the x direction. An optical transport function (OTF) of the system plays an equivalent role as a low pass filter in the spatial frequency domain, and the cut-off $k_x$ determines the diffraction limited resolution. After shifting the $k_x$ distribution by the structured illumination as the last two terms in the above equation 4, high spatial frequencies can be shifted into the range of OTF and detected. For example, in principle, the range of OTF is increased by twice when $k_m$ is on the maximum $k_x$ of the OTF, and, thus, the resolution can be enhanced by, for example, a factor of two beyond the diffraction limit. In order to separate three terms in Eq. 4, several frames of B-scan images are obtained with the illumination/interference pattern shifted. Assuming that the phase shift of the pattern between consequential frames is constant, Eq. 4 can be rewritten as $$\tilde{I}(k_x,n)/I_0 = \tag{Eq. 5}$$
$$\tilde{R}(k_x) + \frac{m}{2}e^{j(n\Delta\phi+\phi_0)}\tilde{R}(k_x-k_m) + \frac{m}{2}e^{-j(n\Delta\phi+\phi_0)}\tilde{R}(k_x+k_m),$$

where $\Delta\phi$ denotes a constant phase shift of the illumination pattern between frames and n=0, 1, 2, ... denotes the frame number. By another FT in terms of the frame number n, second and third terms can be separated from the first term:

$$\tilde{\tilde{I}}(k_x,k_n)/I_0 = \tilde{R}(k_x)\delta(k_n) + \tag{Eq. 6}$$
$$\frac{m}{2}e^{j\phi_0}\delta(k_n-\Delta\phi)\times\tilde{R}(k_x-k_m) + \frac{m}{2}e^{-j\phi_0}\delta(k_n+\Delta\phi)\tilde{R}(k_x+k_m),$$

where $k_n$ and n are Fourier pairs, and the delta functions separate the three terms in the $k_n$ space. The extended spatial frequency can then be shifted to a reciprocal space of the original $\tilde{R}(k_x)$.

As discussed above with respect to FIG. 3B, under a raster linear scan, the temporal modulation is transformed into a spatial illumination pattern. The frequency of the temporal modulation determines the period of the pattern. A cube beamsplitter (BS) forms an open space Michelson interferometer, for example.

A reference arm includes a dispersion control (DC), a mirror and an optical chopper for temporal intensity modulation. In certain examples, a conventional Fourier-domain OCT system is adapted and an optical chopper is installed on the path of the reference arm (FIG. 3B). The illumination comes from a supercontinuum source (e.g., SuperK, NKT) with bandwidth from 650-800 nm, yielding an axial resolution of ~1.5-2 μm in air, for example. A Gaussian focus beam creates the illumination and is steered by the galvo mirror. The theoretical FWHM is 9 μm in air (e.g., single mode field diameter: 4.6 m at 680 nm, 11: f=10 mm, Obj: f=33 mm), for example.

In the example, each B-scan is composed of 256 A-lines (2.56 kHz A-scan rate). The B-scan rate is 10 frames per second (fps) and the period of the illumination pattern is configured to be 12 μm. The sampling interval between adjacent A-lines depends on the fast scanning range. With 250 m scanning range, the A-line interval is 1 μm. The number of modulation periods during one B-scan is non-integer so that a subsequent B-scan(s) can have slight phase shifts of the pattern as the $\Delta\phi$ in Eq. 4. For a better signal to noise ratio (SNR), ten frames can be acquired with the total phase shift equal to $2\pi$, for example.

During data processing, two FT are first performed on x and n according to Eq. 6 to separate the three spatial frequency terms. Secondly, the three spatial frequency terms are multiplied by a top head window with the width of the OTF of the system, and then normalized by the OTF, which is a Gaussian form whose width is determined by the system resolution. Next, the two shifted spatial frequency terms are shifted back by $k_m$. The value of m is estimated by a least-square fitting of an overlapping area of original and shifted spatial frequency distribution.

The value of $\phi_0$ is obtained when $k_x=k_m$ and $k_n=\Delta\phi$ according to Eq. 6. At last, a Tukey window ($\alpha=0.25$) is multiplied on the extended $\tilde{R}(k_x)$ to round out a sharp edge and eliminate high frequency artifacts. A final SIOCT image is then re-transformed into spatial space using the extended spatial frequency distribution $R(k_x)$.

In certain examples, without modifying an illumination beam profile, SIOCT enhances the resolution by a factor of two. A sacrifice is that multiple frames of the same B-scan are used to numerically synthesize an extended spatial frequency distribution. In principle, only three frames with 120 degree phase increment are needed. With a current state-of-the-art high speed OCT system, the A-line rate is over 400 MHz which can make multi-frame collection at the level of 1 ms. Assume allowance of 10 μm drifting, the tolerant motion speed is around 10 mm/s, which can be well satisfied. Therefore, SIOCT can be adapted in real-time imaging and an electro-optic or acousto-optic modulator before the interferometry can be used for fast modulation.

A maximum limit of the temporal modulation frequency is reached when the spatial pattern period is the system resolution. A precise transform from temporal to spatial pattern is to convolute the sinusoidal wave with a point spread function. Thus, when the modulation frequency exceeds the resolution limit, the transform is no longer able to produce a spatially varying pattern. In certain examples, this technique can be combined with other resolution enhancement methods to further improve resolution.

Figure 7:
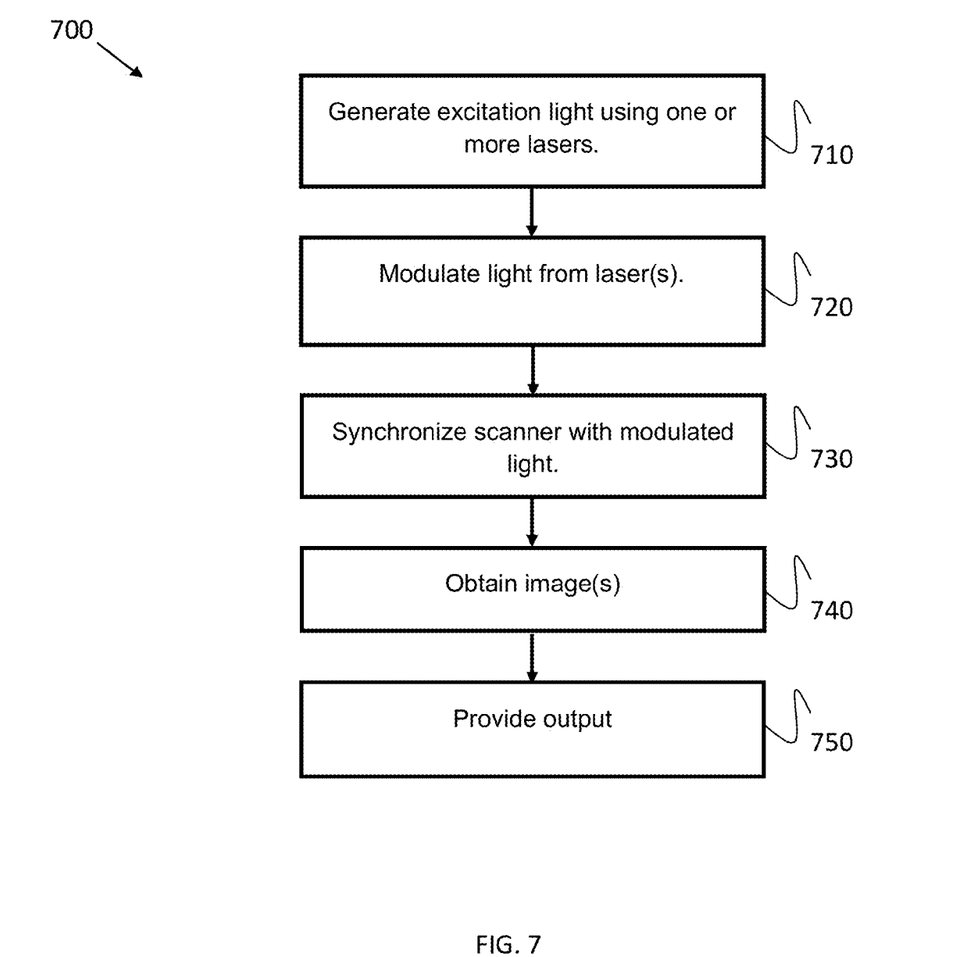
FIG. 7 illustrates a flow diagram of an example method to facilitate laser scanning structured illumination.

FIG. 7 shows a flow diagram of a method 700 representative of example machine readable instructions that can be executed to implement the example systems shown and described herein and/or portions of one or more of those systems. The example processes of FIG. 7 can be performed using a processor, a controller and/or any other suitable processing device. For example, the example processes of FIG. 7 can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIG. 7 can be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIG. 7 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIG. 7 can be implemented manually or as any combination(s) of any of the foregoing techniques, for example, any combination of firmware, software, discrete logic and/or hardware. Further, although the example processes of FIG. 7 are described with reference to the flow diagram of FIG. 7, other methods of implementing the processes of FIG. 7 can be employed. For example, the order of execution of the blocks can be changed, and/or some of the blocks described can be changed, eliminated, sub-divided, or combined.

Additionally, any or all of the example processes of FIG. 7 can be performed sequentially and/or in parallel by, for example, separate processing threads, processors, devices, discrete logic, circuits, etc.

FIG. 7 illustrates a flow diagram of an example method 700 to facilitate laser scanning structured illumination. At block 710, a laser is used as an excitation source to generate light. For example, one or more lasers can be used to provide differing excitations combined using mirrors, etc.

At block 720, light from the laser(s) is modulated. For example, light can be modulated mechanically, electronically, and/or optically using an insert positioned with respect to a laser. For example, an optical chopper can be positioned in the path of light aimed to pass through a sample. The chopper provides temporal intensity modulation to the light (e.g., laser light), for example. As another example, an electro-opto modulator can be installed to modulate light intensity (e.g., in combination with a polarizer).

At block 730, a scanner to obtain an image of an object is controlled to be in synch with the modulated light. For example, a delay can be determined and introduced to time the scanning with the modulating. A second pair of scanner is identically synchronized to project the focal image to image detectors, for example.

At block 740, one or more images are obtained of the object using the modulated light timed with the scanner. A plurality of lenses can focus the light with respect to an x y scanner positioned with respect to the object, for example. Linear and/or non-linear optics may be used to obtain image data, for example. Confocal and other variety of microscopy can be facilitated accordingly, with or without a contrast agent.

At block 750, an output is provided. For example, an image, such as an eye image, deep tissue image, etc., is provided for display, storage, printing, and/or other output. In certain examples, a variety of laser scanning microscopy can be supported accordingly. In certain examples, a scanning microscope is provided with a modulator module to be attached with respect to the scanner to coordinate with the scanner and provide modulation for improved resolution imaging (e.g., two photon detection non-linear imaging), for example.

While example systems have been illustrated in FIGS. 1, 3A-B, and 4, one or more of the elements, processes and/or devices illustrated in FIGS. 1, 3A-B, and 4 can be combined, divided, re-arranged, omitted, eliminated and/or implemented in any other way. Further, one of the more of the elements, processes and/or devices illustrated in the systems 100, 300, 301, 400, and/or, more generally, the example systems 100, 300, 301, 400 can be implemented by hardware, software, firmware and/or any combination of hardware, software and/or firmware. Thus, for example, any of the elements, processes and/or devices illustrated in the systems 100, 300, 301, 400 of FIGS. 1, 3A-B and 4, and/or, more generally, the example systems 100, 300, 301, 400 could be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended apparatus claims are read to cover a purely software and/or firmware implementation, at least one of the components of FIGS. 1, 3A, 3B, and/or 4 is hereby expressly defined to include a computer readable medium such as a memory, DVD, CD, Blu-ray, etc., storing the software and/or firmware. Further still, the example systems 100, 300, 301, and 400 can include one or more elements, processes and/or devices in addition to, or instead of, those illustrated in FIGS. 1, 3A-B, and 4, and/or can include more than one of any or all of the illustrated elements, processes and devices.

Figure 8:
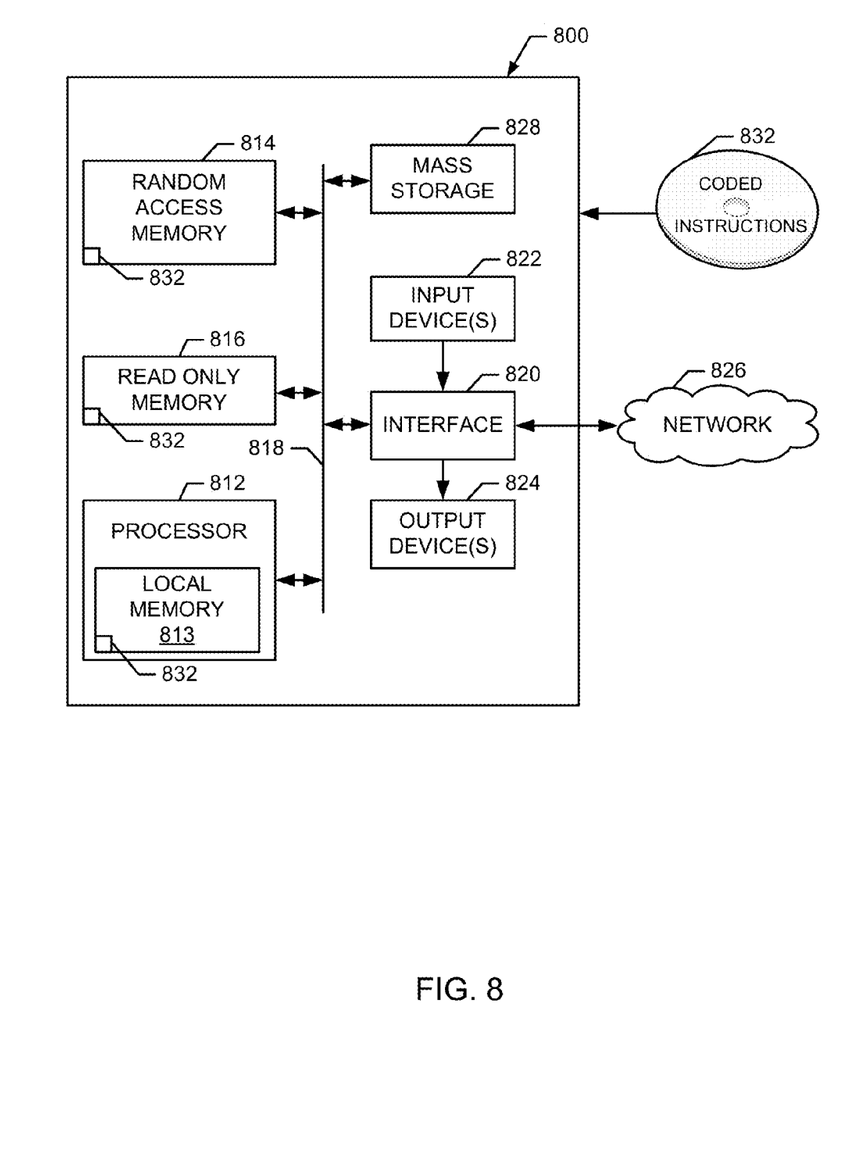
FIG. 8 is a block diagram of an example computer or other processor system that can be used to implement systems, apparatus, and methods described herein.

FIG. 8 is a block diagram of an example processor platform that may be used to execute systems, methods and apparatus described herein. The processor platform 800 of the instant example includes a processor 812. For example, the processor 812 can be implemented by one or more microprocessors or controllers from any desired family or manufacturer. The processor 812 includes a local memory 813 (e.g., a cache) and is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814, 816 is controlled by a memory controller.

The processor platform 800 also includes an interface circuit 820. The interface circuit 820 may be implemented by any type of interface standard, such as an Ethernet interface, a universal serial bus (USB), and/or a PCI express interface.

One or more input devices 822 are connected to the interface circuit 820. The input device(s) 822 permit a user to enter data and commands into the processor 812. The input device(s) can be implemented by, for example, a keyboard, a mouse, a touchscreen, a track-pad, a trackball, isopoint and/or a voice recognition system.

One or more output devices 824 are also connected to the interface circuit 820. The output devices 824 can be implemented, for example, by display devices (e.g., a liquid crystal display, a cathode ray tube display (CRT), etc.). The interface circuit 820, thus, typically includes a graphics driver card.

The interface circuit 820 also includes a communication device such as a modem or network interface card to facilitate exchange of data with external computers via a network 826 (e.g., an Ethernet connection, a digital subscriber line (DSL), a telephone line, coaxial cable, a cellular telephone system, etc.).

The processor platform 800 also includes one or more mass storage devices 828 for storing software and data. Examples of such mass storage devices 828 include floppy disk drives, hard drive disks, compact disk drives and digital versatile disk (DVD) drives. The mass storage device 828 may implement a local storage device.

The coded instructions 832 of FIGS. 1, 3A-3B, 4 and/or 7 may be stored in the mass storage device 828, in the volatile memory 814, in the non-volatile memory 816, and/or on a removable storage medium such as a CD, Blu-Ray, or DVD.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

We claim:

1. A structured illumination microscopy system comprising:
    a laser source to generate excitation illumination directed toward a target object;
    a modulator to modulate the excitation illumination temporally in a controllable, periodic spatial pattern to be constructed on the target object to provide sub-diffractional resolution in a lateral direction with respect to the target object;
    two synchronized laser scanning mirrors in confocal arrangement, the two laser scanning mirrors units to be synchronized and controlled to translate the temporally modulated illumination into the periodic spatial pattern on the target object, a first of the two scanning mirrors to receive the modulated excitation illumination and project the modulated excitation illumination with a controllable phase delay on the target object in periodic spatial pattern by linearly steering a focal spot of the modulated excitation illumination in the lateral direction to transform the modulated excitation illumination into the periodic spatial pattern, wherein tuning of a frequency of the temporal modulation determines a period of the spatial pattern, and a second of the two scanning mirrors to receive emission fluorescence from the target object generated by the periodic spatial pattern of modulated excitation illumination and project the emission fluorescence;
    a detector to collect emission fluorescence from the target object via the second of the two scanning mirrors for processing to form an image; and
    a computing device to control the modulator to modulate the excitation illumination temporally in a controllable, periodic spatial pattern and to control the periodic spatial pattern with respect to the first scanning mirror to enhance lateral resolution beyond a diffraction limit in the image formed based on the emission fluorescence collected from the target object via the second scanning mirror by shifting high spatial frequencies in a Fourier domain into a detectable range to enhance the lateral resolution beyond the diffraction limit, wherein the computing device further controls the modulation of the excitation illumination to include a non-integer number of modulation periods to control the phase delay.

2. The system of claim 1, wherein the modulator comprises an optical chopper.

3. The system of claim 1, wherein the modulator further comprises a mirror.

4. The system of claim 3, wherein the mirror comprises at least one of a galvo mirror, a polygon mirror, and a dichroic mirror.

5. The system of claim 1, wherein the modulator comprises an electro-opto modulator.

6. The system of claim 5, wherein the modulator further comprises a polarizer.

7. The system of claim of 1, wherein the detector comprises a photomultiplier tube.

8. The system of claim 1, wherein the detector comprises a charge coupled device camera.

9. The system of claim 8, wherein the detector further comprises a spectrometer.

10. The system of claim 1, wherein the laser comprises at least one of a pulse laser illumination source and a continuous wave laser.

11. A structured interference optical coherence tomography system comprising:
a laser source to generate excitation illumination directed toward a target object;
a modulator to modulate the excitation illumination temporally in a controllable, periodic spatial pattern to be constructed on the target object to provide sub-diffractional resolution in a lateral direction with respect to the target object;
two pairs of laser scanning mirrors in confocal arrangement, the laser scanning mirrors synchronized and controlled to receive the modulated excitation illumination and project the modulated excitation illumination with a controllable phase delay on the target object by linearly steering a focal spot of the modulated excitation illumination in the lateral direction to transform the modulated excitation illumination into the periodic spatial pattern on the target object, wherein tuning of a frequency of the temporal modulation determined a period of the spatial pattern;
a detector to collect emission illumination from the target object via the two pairs of laser scanning mirrors for processing to form an image; and
a computing device to control the modulator to modulate the excitation illumination temporally in a controllable, periodic spatial pattern and to control the periodic spatial pattern with respect to the laser scanning mirror pairs to enhance lateral resolution beyond a diffraction limit in the image formed based on the emission fluorescence collected from the target object by shifting high spatial frequencies in a Fourier domain into a detectable range to enhance the lateral resolution beyond the diffraction limit, wherein the computing device further controls the modulation of the excitation illumination to include a non-integer number of modulation periods to control the phase delay.

12. The system of claim 11, wherein the modulator comprises an optical chopper.

13. The system of claim 11, wherein the modulator is arranged with respect to at least one of a reference arm, a sample arm, and a beamsplitter.

14. The system of claim 11, wherein the modulator further comprises a mirror arranged with respect to a reference arm to create structured interference for collection by the detector.

15. The system of claim 14, wherein the mirror comprises at least one of a galvo mirror and a polygon mirror.

16. The system of claim 11, wherein the modulator comprises an electro-opto modulator.

17. The system of claim of 11, wherein the detector comprises at least one of a complementary metal oxide silicon camera and a charge coupled device camera.

18. The system of claim 17, wherein the detector further comprises a spectrometer.

19. The system of claim 11, further including a cube beamsplitter associated the laser scanning mirrors.

* * * * *

UNITED STATES PATENT AND TRADEMARK OFFICE
CERTIFICATE OF CORRECTION

PATENT NO.       : 9,360,660 B2
APPLICATION NO.  : 13/902288
DATED            : June 7, 2016
INVENTOR(S)      : Ji Yi et al.

Page 1 of 1

It is certified that error appears in the above-identified patent and that said Letters Patent is hereby corrected as shown below:

In the Claims (Claim 1) Column 14, line 42: between "mirrors" and "to be" delete the word "units".

Signed and Sealed this
Ninth Day of August, 2016

Michelle K. Lee
*Director of the United States Patent and Trademark Office*